(12) United States Patent
Murphy (10) Patent No.: US 10,207,085 B2
(45) Date of Patent: Feb. 19, 2019

(54) MEDICAL DRAINAGE CATHETER WITH BREAK-AWAY TIP AND EXTRALUMINAL RETENTION APPARATUS

(71) Applicant: Timothy Murphy, Providence, RI (US)

(72) Inventor: Timothy Murphy, Providence, RI (US)

( * ) Notice: Subject to any disclaimer, the term of this patent is extended or adjusted under 35 U.S.C. 154(b) by 280 days.

(21) Appl. No.: 15/158,783

(22) Filed: May 19, 2016

(65) Prior Publication Data
US 2017/0333687 A1 Nov. 23, 2017

(51) Int. Cl.
*A61M 25/00* (2006.01)
*A61M 25/02* (2006.01)
*A61M 27/00* (2006.01)

(52) U.S. Cl.
CPC ........ *A61M 27/00* (2013.01); *A61M 25/0074* (2013.01); *A61M 2025/0293* (2013.01)

(58) Field of Classification Search
CPC .......... A61M 25/0017; A61M 25/0067; A61M 25/0074; A61M 2025/0079
See application file for complete search history.

(56) References Cited

U.S. PATENT DOCUMENTS

| | | | | |
|---|---|---|---|---|
| 5,052,998 A * | 10/1991 | Zimmon | A61F 2/94 | 604/530 |
| 5,752,970 A * | 5/1998 | Yoon | A61B 17/3421 | 604/167.03 |
| 6,508,825 B1 * | 1/2003 | Selmon | A61M 29/02 | 604/104 |
| 6,591,472 B1 * | 7/2003 | Noone | A61M 25/0009 | 264/171.13 |
| 6,939,318 B2 * | 9/2005 | Stenzel | A61B 17/3468 | 604/506 |
| 7,041,090 B2 * | 5/2006 | Bolmsjo | A61F 2/0022 | 604/327 |
| 2002/0010476 A1 * | 1/2002 | Mulholland | A61B 17/22031 | 606/108 |
| 2005/0107739 A1 * | 5/2005 | Palma | A61M 25/0097 | 604/104 |
| 2006/0025753 A1 * | 2/2006 | Kubalak | A61M 25/0017 | 604/544 |
| 2007/0060914 A1 * | 3/2007 | Magnusson | A61M 25/04 | 604/544 |
| 2007/0208276 A1 * | 9/2007 | Kornkven Volk | A61M 25/001 | 600/585 |
| 2007/0244440 A1 * | 10/2007 | Pal | A61M 25/0074 | 604/164.13 |
| 2009/0299261 A1 * | 12/2009 | Bognar | A61M 25/0045 | 604/6.16 |
| 2010/0331825 A1 * | 12/2010 | Hakky | A61M 25/0017 | 604/544 |
| 2011/0152842 A1 * | 6/2011 | Graffam | A61M 25/0052 | 604/540 |
| 2011/0313404 A1 * | 12/2011 | Amos | A61F 2/95 | 604/544 |

(Continued)

*Primary Examiner* — Susan S Su (57) ABSTRACT

The invention features is an embodiment of a drainage catheter to be used to drain fluid or gas from any body space with an improved distal tip of variable configuration, to facilitate passage of a guide wire used for catheter exchange. The invention also features an embodiment of a retention mechanism used to stabilize the drainage catheter in the body, where in this embodiment the retention mechanism is located outside of the lumen of the tube as it courses from its distal attachment sites to the catheter hub.

6 Claims, 8 Drawing Sheets

(56) References Cited

U.S. PATENT DOCUMENTS

| | | | |
|---|---|---|---|
| 2012/0083740 A1* | 4/2012 | Chebator | A61M 25/0074 604/164.03 |
| 2014/0336624 A1* | 11/2014 | Adams, Jr. | A61M 25/0017 604/544 |
| 2015/0343171 A1* | 12/2015 | Hannon | A61M 25/0017 604/544 |
| 2017/0065793 A1* | 3/2017 | Scarpine | A61M 25/0074 |
| 2018/0043135 A1* | 2/2018 | Chen | A61M 25/04 |

* cited by examiner

MEDICAL DRAINAGE CATHETER WITH BREAK-AWAY TIP AND EXTRALUMINAL RETENTION APPARATUS

FIELD

The present invention relates to devices for performing surgical procedures, and in particular to methods and devices for draining fluid or gas from spaces in the body.

BACKGROUND OF THE INVENTION

Medical drainage catheters placed over guide wires have been used for over 40 years to drain fluid or air from various body cavities. Some applications for over-the-wire medical drainage catheters include placement within the thorax for drainage of gas to treat pneumothorax, placement within the thorax to drain fluid, placement within abscesses to drain purulent fluid, placement within the urinary tract to drain urine or purulent fluid in cases of urinary tract obstruction, and placement within the biliary tree to drain bile or purulent fluid in cases of biliary obstruction.

Although medical tube drainage is effective at curing some of these conditions, very often chronic tube drainage is required either indefinitely or permanently. In order to optimize normal function of tube drainage catheters, they are usually put on a maintenance schedule where they are changed at routine intervals. The most frequent way that tube drainage catheters are changed is by placing a guidewire through their lumens and out their distal tips, then removing the old catheter, then introducing the new catheter into the body over the guidewire, then removing the guidewire. However, a considerable limitation of chronic tube drainage is blockage of the distal end due to inspissation or precipitation of proteinaceous or mineral debris, which happens frequently when tubes are left in place chronically. When this happens, it may be impossible to pass the guide wire through the lumen of the drainage catheter and out of its tip. In some cases, there may be compaction of the retention suture down the lumen of the drainage tube as the guidewire is advanced, further narrowing the opening at the catheter tip and impeding passage of the guide wire out of the catheter tip. The present invention offers a solution that enables routine drainage tube exchange over a guide wire by allowing easier passage of the guidewire through the tip of the drainage catheter.

In one embodiment of such a modified tube drainage catheter, the tip of the catheter has a variable configuration, such that it is tapered and cone-shaped as it is introduced into the body, but under pressure of guide wire passage can, if resistance is met, alter its configuration to that its distal opening is wider than its original configuration. One way to achieve a distal tip with a variable lumen diameter would be to fashion longitudinal slits through the wall of the drainage catheter at the distal tip, which could then widen as a guide wire was passed when it meets resistance. Another possible way to achieve a tip with a variable opening would be to place numerous perforations through the material at the tip, rendering it mechanically weak and allowing a guide wire to perforate the material at the tip without passing out of the endhole. Another embodiment of a variable opening at the tip would be to have very thin catheter material at the tip, such that advancement of the guide wire against resistance at the tip would rupture the material when guide wire resistance is met, allowing the guide wire to exit the catheter at or near the tip end.

Another feature of an embodiment of the invention is that any suture wires or retention mechanism are outside of the lumen of the drainage catheter as the catheter exits the body space to be drained, and remain external to the catheter lumen as the catheter exits the body. Using such an embodiment of a drainage catheter retention system, the retaning sutures can be removed entirely from the device prior to placement of the guidewire, eliminating the possibility of the retaining sutures from being compacted within the catheter lumen by advancement of a guide wire through the lumen.

We reference the following U.S. patent documents:
WO2015194837A1
WO2014159431A1
WO2011066113A1
US20140276655A1
US20130274783A1
US20130231639A1
US20120203064A1
US20110295237A1
US20110152842A1
US20100121288A1
US20070049906A1
US20030144636A1
US20010049494A1
U.S. Pat. No. 8,808,261B2
U.S. Pat. No. 8,496,645B2
U.S. Pat. No. 8,496,644B2
U.S. Pat. No. 5,489,269
U.S. Pat. No. 5,308,318
U.S. Pat. No. 4,787,892
U.S. Pat. No. 4,705,510
U.S. Pat. No. 4,693,703
U.S. Pat. No. 4,645,490
U.S. Pat. No. 4,643,720
U.S. Pat. No. 4,610,660

SUMMARY

The devices disclosed herein generally involve a medical tube drainage catheter with a break-away tip and a retention apparatus that can't get compacted within the lumen of the drainage catheter when a guide wire is advanced through it.

In one aspect, the medical tube drainage catheter has a break-away tip comprising a tapered tip that has been structurally altered to make it vulnerable to rupture or perforation by a guide wire that is advanced against resistance at the tip end of the catheter.

In another example, the medical tube drainage catheter has a retaining apparatus that connects the distal catheter within a body space to the proximal hub end of the drainage catheter external to the body while extending across the length of the main shaft of the drainage tube outside of the lumen of the drainage tube.

BRIEF DESCRIPTION OF THE DRAWINGS

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

DETAILED DESCRIPTION OF THE PREFERRED EMBODIMENT

Referring to the drawing figures, like reference numerals designate identical or corresponding elements throughout the several figures. The singular forms "a," "an," and "the" include plural referents unless the context clearly dictates otherwise. Thus, for example, reference to "a solvent" includes reference to one or more of such solvents, and reference to "the dispersant" includes reference to one or more of such dispersants.

Figure 1:
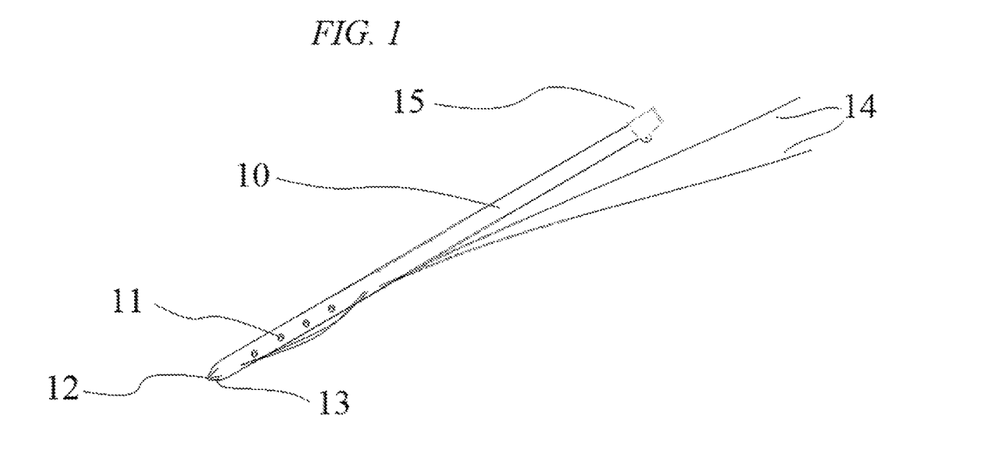
FIG. 1 shows an illustrative embodiment of the drainage catheter in its initial, pre-insertion configuration.
Figure 2:
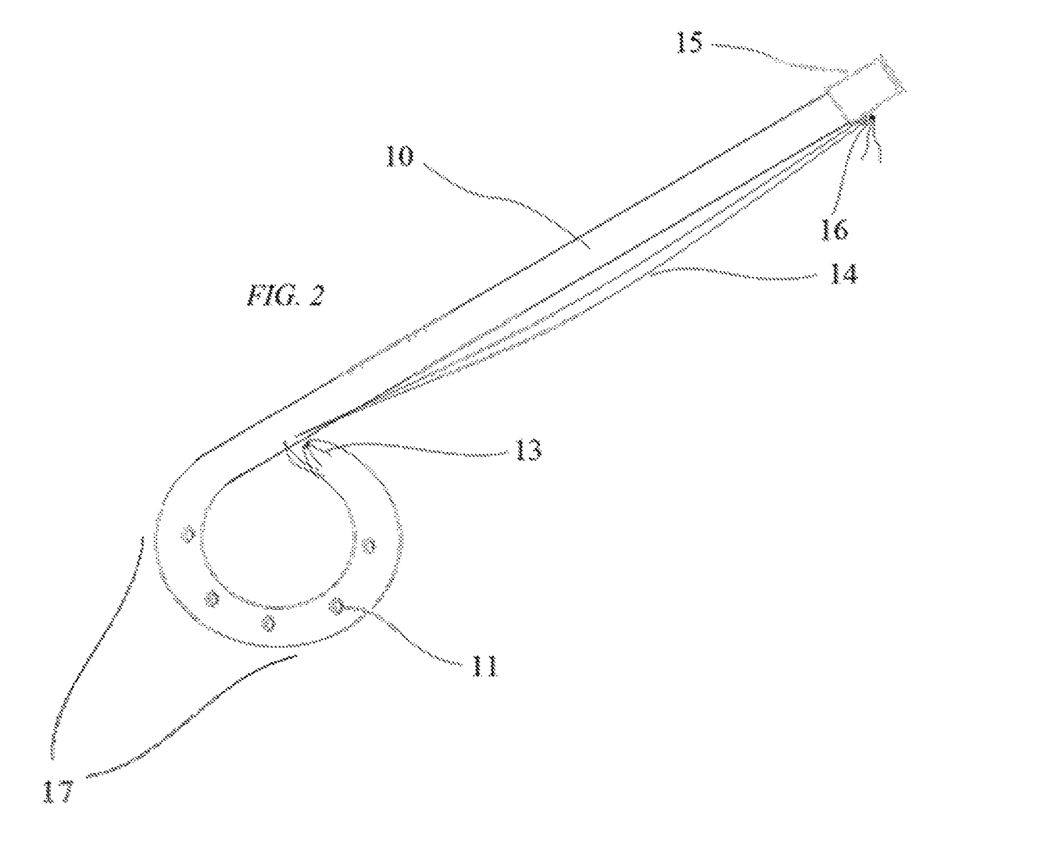
FIG. 2 shows an illustrative embodiment of the drainage catheter in its final, post-insertion, formed configuration.

According to one embodiment of the drainage catheter, as shown in FIG. 1, the tube drainage catheter comprises a hollow tube with a proximal hub 15, a distal tip 12, one or more side holes at a distal section of the catheter 11, loop-forming suture elements 14, and a loop-forming fastener element on the hub 16. FIG. 1 shows one embodiment of the drainage catheter in its straight configuration, which is a configuration that would be suitable for insertion into a space within the body. FIG. 2 is an illustrative example of the drainage catheter in its deployed configuration, with an exemplary mechanical reconfiguration 17 of a distal part of the drainage catheter to impede retraction of the drainage catheter out of the space within the body, in this case shown as a loop. FIG. 2 also shows retaining elements 14 that maintain the mechanical deformation of a distal part of the drainage catheter, in this example secured to a fastening element 16, shown here as an eye loop, on the proximal part of the drainage catheter.

Figure 3:
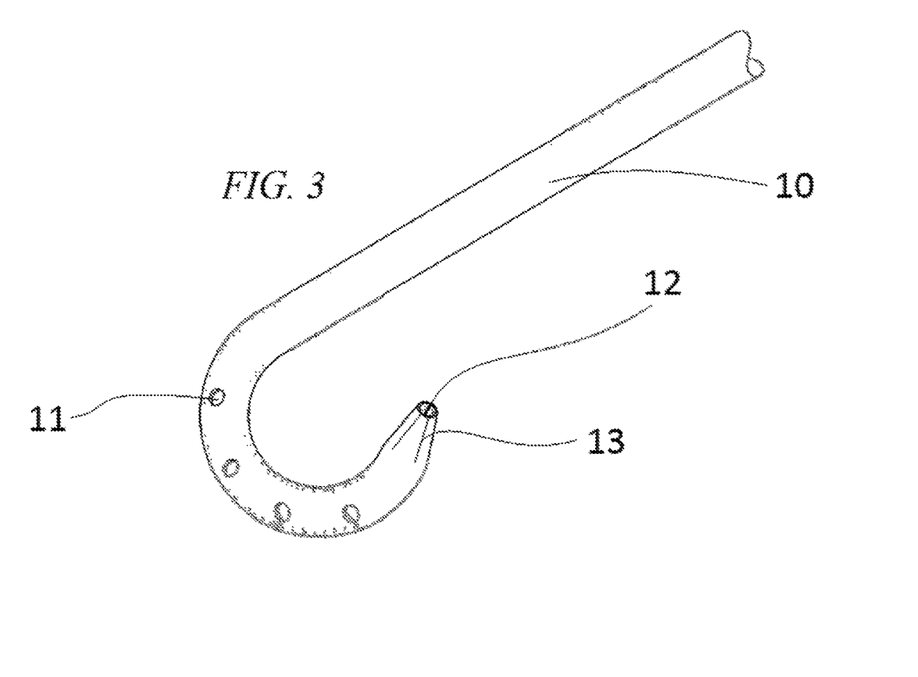
FIG. 3 is one view of the tip of the preferred embodiment of the tip of the catheter in its intact configuration.
Figure 4:
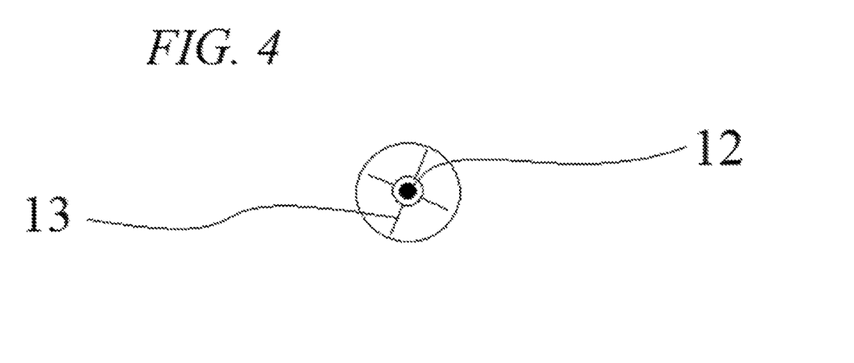
FIG. 4 is an end-on view of the tip of the preferred embodiment of the tip of the catheter in its intact configuration.

FIG. 3 emphasizes one embodiment of the break-away tip configuration, in this case comprising incisions or slits 13 that are present at intervals at the distal end or catheter tip, arranged longitudinally or in some other manner, that allow the tip to change configuration under some mechanical force so that it comprises a larger tip diameter or so that it more readily permits the passage of a guidewire. FIG. 4 shows one embodiment of these incisions or slits 13, in this one example being longitudinally arrayed around the distal catheter endhole 12.

Figure 5:
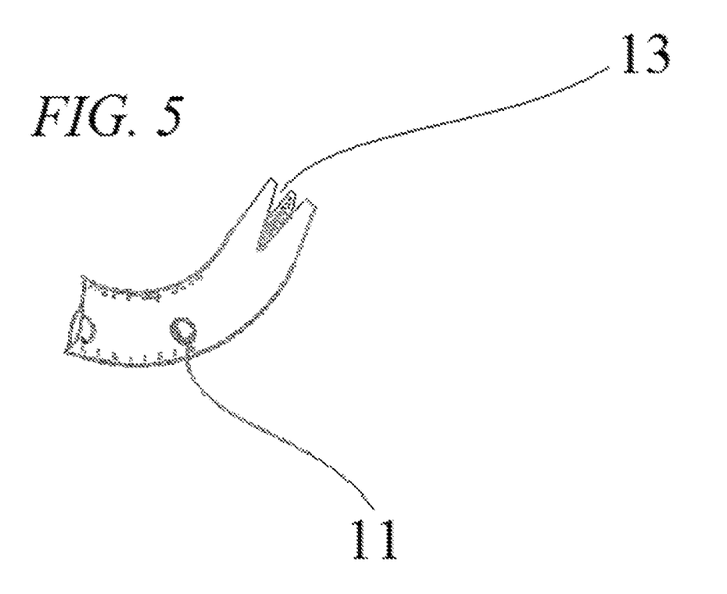
FIG. 5 is one view of the tip of the preferred embodiment of the tip of the catheter showing an example of the tip in its break-away configuration.
Figure 6:
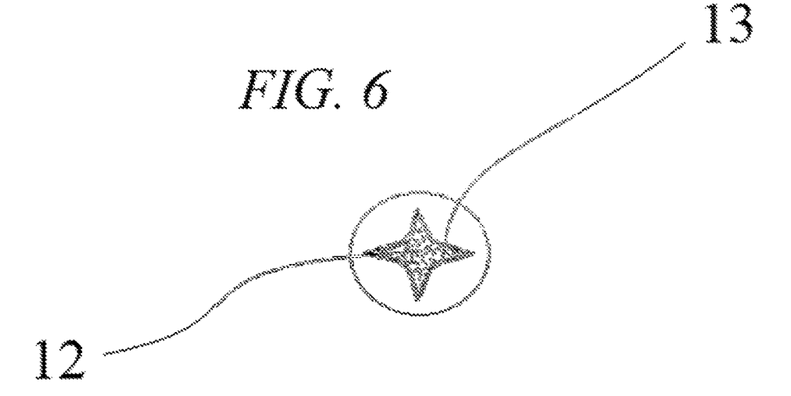
FIG. 6 is an end-on view of the tip of the preferred embodiment of the tip of the catheter in its break-away configuration.

FIG. 5 is one embodiment of how the tip configuration might be altered upon mechanical manipulation so that any incisions or slits 13 assume an alternate shape or configuration such that the guide wire pathway or lumenis enlarged through the tip of the tube. FIG. 6 is an end-on view of one embodiment of the tip of the catheter showing an example of the tip in its altered configuration, with widening or separation of catheter tip elements 13 as might occur with mechanical manipulation, to enlarge the lumen at the tip of the catheter.

Figure 7:
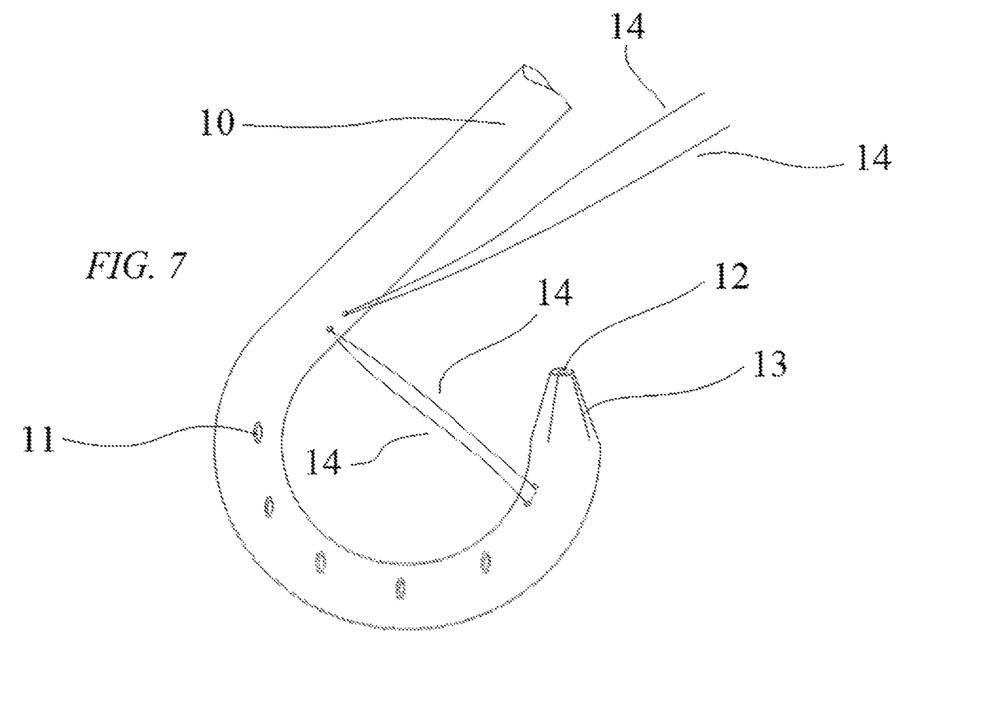
FIG. 7 is one view of the distal tip of the invention showing one embodiment of the loop retention sutures.

FIG. 7 shows one example of how elements 14 that change the configuration of a distal part of the catheter tip so that the catheter tip resists retraction from the body are routed through parts of the distal end of the catheter in a redundant way, with retaining element not traveling outside of the space to be drained within the body within the lumen of the drainage catheter. In this embodiment shown in FIG. 7, the retaining elements 14 for the distal tip retention configuration run alongside of the drainage catheter and outside of its lumen as the tube exits the space in the body to be drained, through soft tissues of the body, and out through the skin.

Figure 8:
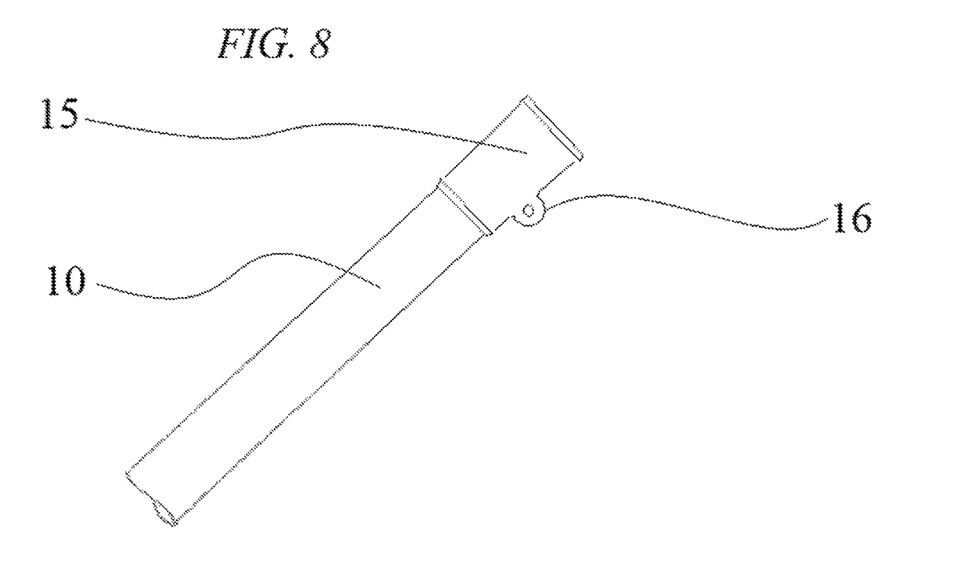
FIG. 8 is one view of the hub of one embodiment of the invention prior to insertion.
Figure 9:
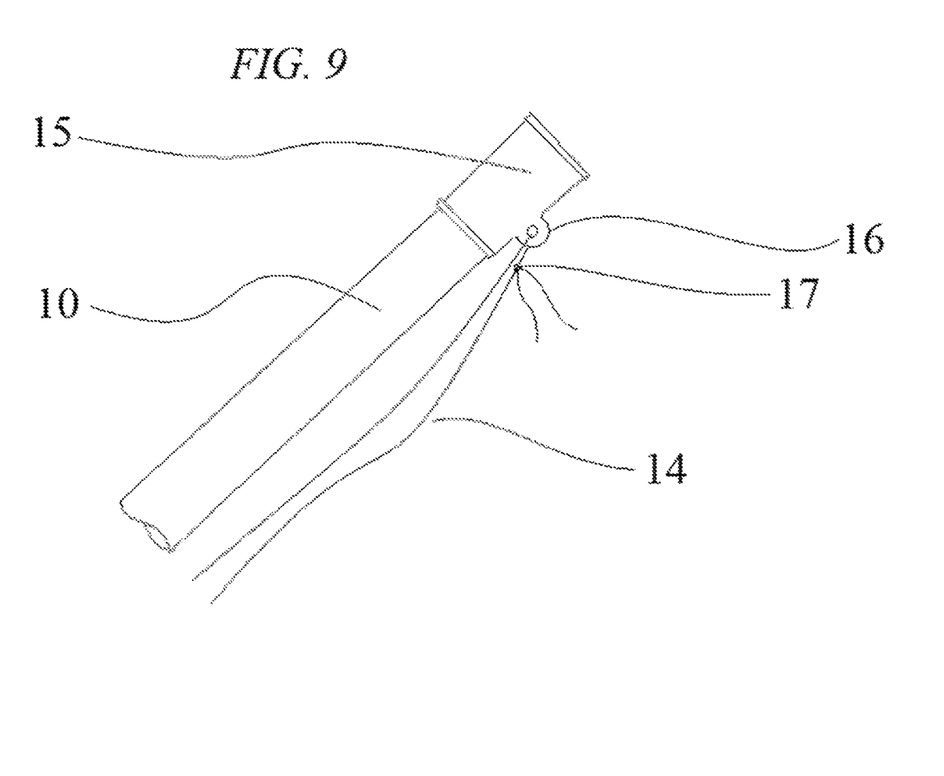
FIG. 9 is one view of the hub of one embodiment of the invention showing an example of suture anchoring after insertion of the catheter.

FIG. 8 shows an embodiment of a fastener 16 on the proximal end of the drainage catheter that permits attachment of the distal end retaining elements 14. FIG. 9 shows an embodiment of proximal end retaining elements attached to an example of a fastener 14 at the proximal end of the catheter.

What is claimed is:

1. A medical drainage catheter comprising:
   a hollow central lumen through a shaft of the drainage catheter,
   a hub end that is external to a body of a patient and can be attached to a fluid management system,
   a tapered distal tip end formed of a material, said distal tip end having a distal end hole with an original configuration and a second expanded configuration actuated by passage of a guide wire there through when blockage of the distal end hole is present, said guide wire having a diameter not greater than the diameter of the distal end hole in said original configuration.

2. The medical drainage catheter of claim 1, wherein the guide wire actuates the second configuration by widening of one or more incisions or slits in the material at the distal tip end.

3. The medical drainage catheter of claim 1, wherein the guide wire actuates the second configuration by penetration of one or more perforations in the material at the distal tip end.

4. The medical drainage catheter of claim 1, wherein the material of the distal tip end is thinner than a material forming the shaft, such that the guide wire actuates the second configuration by rupturing the material of the distal tip end while advancing through the shaft toward the distal end hole.

5. A medical drainage catheter system comprising a drainage catheter, wherein the drainage catheter, after placement in an organ or cavity within the body of a patient, comprises a loop or another shape at its distal end that helps to retain the drainage catheter within the body, said loop or another shape being achieved by a retention apparatus that passes from the proximal end of the loop to a proximal end of the drainage catheter, said retention apparatus extending from within the organ or cavity to exterior of the body while residing exterior to any component of said drainage catheter system between the loop and the hub.

6. The medical drainage catheter of claim 5, wherein the retention apparatus runs through connection anchor points on the drainage catheter but is reversibly attached to those anchor points, such that the retention apparatus can be completely removed from the drainage catheter while the drainage catheter is indwelling within the body of the patient.

\* \* \* \* \*